United States Patent [19]

Effenberger et al.

[11] 4,440,686

[45] Apr. 3, 1984

[54] 2-AZIDO-3-BENZYLOXY-PROPIONIC ACID-BENZYL ESTER, PROCESS FOR ITS PRODUCTION AND ITS USE

[75] Inventors: Franz Effenberger, Stuttgart; Gerhard Zoller, Maintal, both of Fed. Rep. of Germany

[73] Assignee: Degussa Aktiengesellschaft, Frankfurt, Fed. Rep. of Germany

[21] Appl. No.: 411,323

[22] Filed: Aug. 25, 1982

[30] Foreign Application Priority Data

Sep. 10, 1981 [DE] Fed. Rep. of Germany ....... 3135840

[51] Int. Cl.³ .......................................... C07C 117/00
[52] U.S. Cl. .................... 260/349; 560/170; 560/60; 562/567; 260/453.7
[58] Field of Search ................ 260/349; 562/567; 560/170

[56] References Cited

U.S. PATENT DOCUMENTS 3,471,523  10/1969  Harvey ............................... 260/349

3,880,922   4/1975  Reinhold ..................... 260/465.4 X
3,914,261  10/1975  Parker et al. ...................... 260/349

OTHER PUBLICATIONS

C. A., 96, (1982); Effenberger et al., 96:181591u.

*Primary Examiner*—Joseph P. Brust
*Attorney, Agent, or Firm*—Cushman, Darby & Cushman

[57] ABSTRACT

The subject matter of the invention is the new 2-azido-3-benzyloxy-propionic acid benzyl ester which is a valuable intermediate product for the production of D,L-serine or derivatives of D,L-serine. The new compound is produced by reacting 2-chloroacrylonitrile with twice the molar amount of benzyl alcohol to form 3-benzyloxy-2-chloropropionic acid imino benzyl ester, saponifying this with acid to form 3-benzyloxy-2-chloropropionic acid benzyl ester, and finally exchanging the chlorine atom by means of an alkali metal azide in the presence of a phase transfer catalyst for an azido group.

4 Claims, No Drawings

2-AZIDO-3-BENZYLOXY-PROPIONIC ACID-BENZYL ESTER, PROCESS FOR ITS PRODUCTION AND ITS USE

SUMMARY OF THE INVENTION

The subject matter of the invention is the benzyl ester of 2-azido-3-benzyloxypropionic acid and a process for its production which is characterized by reacting 2-chloroacrylonitrile with double the molar amount of benzyl alcohol to form the iminobenzyl ester of 3-benzyloxy-2-chloropropionic acid, saponifying this with acid to form the benzyl ester of 3-benzyloxy-2-chloropropionic acid and finally exchanging the chlorine atom for an azido group by means of an alkali metal azide in the presence of a phase transfer catalyst.

The new benzyl ester of 2-azido-3-benzyloxypropionic acid can be subjected to catalytic hydrogenation whereby the azido group is reduced to an amino group. According to the reaction conditions used thereby there can be obtained directly at will e.g. D,L-serine, O-benzyl-D,L-serine, O-benzyl-D,L-serine benzyl ester or an alkyl ester of D,L-serine, e.g. the methyl ester, ethyl ester or butyl ester, or the corresponding hydrochloride.

Accordingly, the benzyl ester of 2-azido-3-benzyloxypropionic acid is a valuable key substance for the production of D,L-serine and derivatives of D,L-serine.

The process of the invention for the production of 2-azido-3-benzyloxypropionic acid benzyl ester starts from the cheap, stable and industrially nice to handle 2-chloroacrylonitrile and proceeds in all reaction steps with high yields. Moreover, in the further processing to D,L-serine or derivatives of D,L-serine high yields are produced.

In the first step of the reaction of 2-chloroacrylonitrile is reacted with at least double the molar amount of benzyl alcohol. It is especially advantageous to use benzyl alcohol in excess, especially in a molar amount of 2.1 to 10 moles per mole of 2-chloroacrylonitrile employed. The reaction takes place under the catalytic influence of an alkali metal benzylate, e.g. sodium benzylate or potassium benzylate, which is added as such or can be formed in situ from an alkali metal and benzyl alcohol. Especially preferred, is the use of sodium benzylate. The alkali metal benzylate is suitably added in an amount of 0.5 to 50 mole percent based on the 2-chloroacrylonitrile employed, preferably in an amount of about 5 mole percent.

The suitable temperature range for the reaction is between $-35°$ and $+80°$ C., especially between $0°$ and $+5°$ C. In this first reaction step the 2-chloroacrylonitrile is converted into 3-benzyloxy-2-chloropropionic acid iminobenzyl ester, which can be isolated after neutralization of the crude reaction mixture with carbon dioxide by fractional distillation at reduced pressure. However, its isolation is not absolutely necessary, but rather the crude reaction mixture can be directly further processed.

In the second reaction step then the crude, or through distillation purified, 3-benzyloxy-2-chloropropionic acid iminobenzyl ester is saponified in the presence of a mineral acid, e.g. hydrochloric acid, sulfuric acid or phosphoric acid. A particularly suitable saponification agent is about 10 weight percent aqueous hydrochloric acid. Suitably, the saponification takes place at room temperature, and generally is complete in at most one hour. The 3-benzyloxy-2-chloropropionic acid benzyl ester formed is extracted from the crude saponification mixture, e.g. with diethyl ether, and after drying the extract, for example with magnesium sulfate, is obtained in pure form by fractional distillation at reduced pressure.

Finally, in a third reaction step, the chlorine atom of the 3-benzyloxy-2-chloropropionic acid benzyl ester is exchanged for an azido group with an alkali metal azide, e.g. sodium azide, potassium azide or lithium azide. The alkali metal azide, preferably sodium azide, is added in the form of an aqueous solution. Since, to avoid undesired side reactions, the reaction suitably is carried out at a relatively low temperature in the range between room temperature and 100° C., for example at about 60° C., the presence of a phase transfer catalyst is necessary. There are suited all of the phase transfer catalysts known in the literature, such as quaternary ammonium and phosphonium salts, e.g. trihexyl methyl ammonium chloride, trioctyl methyl ammonium bromide, trioctyl methyl phosphonium chloride, and crown ethers. Particularly preferred are quaternary ammonium salts, especially a commercial tri-($C_8$ to $C_{10}$—alkyl)-methylammonium chloride ("Tricaprylylmethylammonium chloride"; Aliquat 336). The phase transfer catalyst is suitably used in an amount of about 5 mole percent based on the benzyl ester of 3-benzyloxy-2-chloropropionic acid employed, but this amount can be varied. The alkali metal azide is suitably employed in excess, for example in 1.1 to 1.5 times the theoretically required amount. The exchange of the chlorine atom for the azide group generally requires a reaction time of 8 to 10 hours. The isolation of the 2-azido-3-benzyloxypropionic acid benzyl ester advantageously takes place in such a manner that the crude reaction mixture is extracted several times with methylene chloride, the combined extracts dried, for example with magnesium sulfate, and a chromatographic separation carried out in a silica gel column. There is especially suited as running agent for the separation, a mixture of 15 parts by volume of petroleum ether, and 1 part by volume of ethyl acetate.

Surprisingly, in this chromatographic separation, all impurities or byproducts are so firmly held in the silica gel column that the eluate after the vaporization, suitably at reduced pressure, yields a colorless oil, which according to its elemental analysis and spectroscopic data consists of pure 2-azido-3-benzyloxypropionic acid benzyl ester.

This new compound serves as a valuable intermediate product for the production of D,L-serine, D,L-serine hydrochloride, D,L-serine methyl ester hydrochloride, D,L-serine ethyl ester hydrochloride, O-benzyl-D,L-serine benzyl ester hydrochloride or O-benzyl-D,L-serine.

To produce D,L-serine, the 2-azido-3-benzyloxypropionic acid benzyl ester is dissolved in an inert solvent, for example, acetone, and treated with dry gaseous hydrogen chloride. The gaseous hydrogen chloride is added in at least an equimolar amount, however, it can also be used in an excess up to about 10:1 on a molar basis.

Then, after addition of a palladium catalyst, the material is hydrogenated in an autoclave until there has been complete reaction. As palladium catalysts there can be employed, e.g. finely divided palladium black, or palladium compounds such as palladium chloride, palladium bromide, palladium iodide, palladium nitrate, palladium oxide or palladium oxide hydrate or palladium complex salts, such as tetrachloropalladates or hexachloropalladates. Especially preferred, is the use of a palladium catalyst in the form of a carrier catalyst. Suitable carrier materials, for example, are silica gels, aluminum oxide, zeolites, barium sulfate or calcium carbonate. The carrier preferably is activated carbon.

The palladium catalyst is suitably used in an amount between 0.001 and 5 weight percent, calculated as active metal, and based on the weight of the 2-azido-3-benzyloxypropionic acid benzyl ester, preferably in an amount between 0.1 and 1.0 weight percent. The hydrogen pressure in the hydrogenation can be chosen between 1 and 100 bar, preferably between 1 and 80 bar. The hydrogenation can be undertaken at a temperature between 0° and 100° C., preferably between 20° and 80° C.

After the end of the taking up of hydrogen the catalyst together with the D,L-serine hydrochloride is filtered off, and the filtrate discarded. The filter residue is extracted with hot water, and the extract concentrated, for example in a rotary evaporator. The residue obtained is subsequently neutralized with ammonia. After addition of ethanol and cooling pure D,L-serine precipitates. It is filtered off and can be dried under reduced pressure, suitably at a temperature between 25° and 60° C.

Alternatively, for the production of D,L-serine, the process can be carried out in such manner that the 2-azido-3-benzyloxypropionic acid benzyl ester is dissolved in an inert solvent, for example ethanol, and without addition of hydrogen chloride gas, is first hydrogenated at a temperature between 10° and 30° C. at a hydrogen pressure between 30 and 50 bar in the stated manner with the palladium catalyst. Then, the mixture is diluted with water, a further portion of the palladium catalyst added, and hydrogenation continued at a temperature between 60° and 80° C., and a hydrogen pressure between 40 and 70 bar until complete reaction. The amount of water suitably should correspond to about half the volume of the ethanol used, the additional catalyst portion to about half the amount originally added. After the end of the uptake of hydrogen, the catalyst is filtered off, the filtrate evaporated, and the D,L-serine obtained as solid residue dried at reduced pressure and a temperature of about 50° C.

For the production of D,L-serine hydrochloride, the 2-azido-3-benzyloxypropionic acid benzyl ester is hydrogenated as described above after addition of hydrogen chloride gas. After the ending of the hydrogen uptake, the catalyst together with the D,L-serine hydrochloride formed is filtered off and the filtrate discarded. The filter residue is extracted with hot water, and the extract evaporated. The oily residue remaining is brought to crystallization by addition of diethyl ether. The crystals formed of pure D,L-serine hydrochloride are filtered off with suction and dried at reduced pressure, and a temperature of about 50° C.

For the production of D,L-serine alkyl ester hydrochlorides, the process is carried out in such a manner that the 2-azido-3-benzyloxypropionic acid benzyl ester is dissolved in the particular alkanol, e.g. methanol or ethanol, and treated with an excess of hydrogen chloride gas. Then again, as described above, the product is hydrogenated in the presence of a palladium catalyst, but suitably at a temperature between 20° and 30° C. and a hydrogen pressure between 10 and 30 bar.

After the end of the uptake of hydrogen the catalyst is filtered off, the filtrate concentrated and the residue remaining recrystallized from a mixture of about equal parts by volume of alkanol, e.g. ethanol, and diethyl ether. In this manner, there is obtained the pure D,L-serine alkyl ester hydrochloride.

O-benzyl-D,L-serine benzyl ester hydrochloride can be obtained from the 2-azido-3-benzyloxypropionic acid benzyl ester by hydrogenation in ethanol as solvent after addition of an at least equimolar amount of hydrogen chloride gas, but employing as catalyst in place of a palladium catalyst rhenium (VII) sulfide in an amount between 0.001 and 20 weight percent, based on the weight of the 2-azido-3-benzyloxypropionic acid benzyl ester. The reaction temperature again suitably should be between 20° and 30° C., the hydrogen pressure between 10 and 30 bar.

After the end of the hydrogen uptake the catalyst is filtered off and the filtrate evaporated. The residue remaining is taken up in chloroform, and the O-benzyl-D,L-serine benzyl ester hydrochloride precipitated by addition of diethyl ether. For further purification, it can be recrystallized from a mixture of ethanol and diethyl ether.

O-benzyl-D,L-serine can be obtained by hydrogenating the 2-azido-3-benzyloxypropionic acid benzyl ester in ethanol as solvent and hydrogenating in the presence of a palladium catalyst in the amounts given above either without using excess pressure or at a hydrogen pressure up to 40 bar at a temperature between 10° and 30° C.

After the end of the hydrogen uptake, the product is filtered and the filtrate discarded. The residue on the filter is extracted with hot water, and the extract evaporated under reduced pressure. The precipitated O-benzyl-D,L-serine is filtered off with suction, and dried under reduced pressure at about 50° C.

The production of 2-azido-3-benzyloxypropionic acid benzyl ester and its further working up to D,L-serine or various derivatives of D,L-serine is explained in more detail in the following examples.

Unless otherwise indicated, all percentages and parts are by weight.

The process can comprise, consist essentially of or consist of the stated steps with the materials recited.

EXAMPLE 1

0.23 grams (0.01 mole) of sodium were dissolved in 108.14 grams (1.0 mole) of benzyl alcohol. There was slowly dropped into this freshly prepared sodium benzylate solution in benzyl alcohol 17.50 grams (0.20 mole) of 2-chloroacrylonitrile at 0° C. After the end of the dropping in, there was employed poststirring for 1 hour at 0° C. and a further 2 hours at room temperature. The reaction mixture was treated with 60 ml of diethyl ether and then there were dropped in with vigorous stirring 60 ml of 10% hydrochloric acid. Subsequently, there was additional stirring for a further hour at room temperature. The aqueous phase was extracted three times, in each case with 50 ml of diethyl ether, and the combined organic phases dried with magnesium sulfate. After vaporization of the solvent there was obtained an 87% yield of crude 3-benzyloxy-2-chloropropionic acid benzyl ester. After fractionation in a vacuum, there were obtained 43.9 grams (72% of theory) of pure 3-benzyloxy-2-chloropropionic acid benzyl ester having a boiling point of 153°–155° C. at 0.0065 mbar.

$\eta_D^{20}$: 1.5472

IR (liquid capillary): 1740 (C=O) cm$^{-1}$
$C_{17}H_{17}ClO_3$ (304.776)
Calculated: C: 67.00%; H: 5.62%; Cl: 11.63%; Found: C: 67.19%; H: 5.67%; Cl: 11.37%.

EXAMPLE 2

(a) Production of 3-Benzyloxy-2-chloropropionic acid iminobenzyl ester 0.23 grams (0.01 mole) of sodium were dissolved in 108.14 grams (1.0 mole) of benzyl alcohol. To this freshly prepared sodium benzylate solution in benzyl alcohol, there were slowly dropped in at 5° C. 17.50 grams (0.20 mole) of 2-chloroacrylonitrile. Then there was post stirring for 1 hour at 5° C. and for a further 2 hours at room temperature. Carbon dioxide was led into the reaction solution, the precipitated solid material filtered off, and the filtrate fractionated in a vacuum. 48.6 grams of pure 3-benzyloxy-2-chloropropionic acid imino-benzyl ester came over at 150°–154° C., at a pressure of 0.0065 mbar.

$\eta_D^{20}$: 1.5569

IR (liquid capillary): 1660 (C=N); 3315 (N—H) cm$^{-1}$ $C_{17}H_{18}ClNO_2$ (303.79)
Calculated: C: 67.21%; H: 5.97%; Cl: 11.67%; N: 4.61%; Found: C: 67.47%; H: 6.04%; Cl: 11.44% N: 4.81%.

(b) Saponification of the 3-Benzyloxy-2-chloropropionic acid iminobenzyl ester 15.19 grams (0.05 mole) of 3-benzyl-oxy-2-chloropropionic acid iminobenzyl ester were stirred in 30 ml of 10% hydrochloric acid for 1 hour at 25° C. Then, the reaction mixture was extracted twice, each time with 20 ml of diethyl ether, washed neutral with a sodium bicarbonate solution, and the ether phase dried over magnesium sulfate. After vaporization of the ether, the product was fractionated in a vacuum.

There were obtained 13.1 grams (86% of theory) of pure 3-benzyloxy-2-chloropropionic acid benzyl ester having a boiling point of 153°–155° C. at 0.0065 mbar.

EXAMPLE 3

4.57 grams (0.015 mole) of the 3-benzyloxy-2-chloropropionic acid benzyl ester obtained according to Example 1 or 2 were added to a solution of 1.46 grams (0.0225 mole) of sodium azide in 6 ml of water. After addition of 0.31 grams (5 mole percent) of Aliquat 336 as phase transfer catalyst the mixture was held at 60° C. for 9 hours under intensive stirring. It was extracted three times, each time with 15 ml of methylene chloride, the combined extracts were dried over magnesium sulfate, the methylene chloride was vaporized, and the residue purified via a 40 cm silica gel column with the running agent petroleum ether/ethyl acetate (volume ratio 15:1).

After vaporizing the eluate under reduced pressure there were obtained 3.83 grams 82% of theory) of 2-azido-3-benzyloxpropionic acid benzyl ester as a colorless oil.

$\eta_D^{20}$: 1.5458

IR (liquid capillary): 1745 (C=O); 2100 (Azide)cm$^{-1}$
$C_{17}H_{17}N_3O_3$ (311.34)
Calculated: C: 65.58%; H: 5.50%; N: 13.50%; Found: C: 65.39%; H: 5.60%; N: 13.60%.

EXAMPLE 4

1.56 grams (0.005 mole) of 2-azido-3-benzyloxypropionic acid benzyl ester were dissolved in 10 ml of absolute acetone, 0.90 grams (0.025 mole) of dry hydrogen chloride gas led in and there was added to this solution 0.20 grams of palladium on activated carbon (10%). This reaction mixture was hydrogenated in an autoclave for 20 hours at a hydrogen pressure of 20 bar, and a reaction temperature of 25° C. After filtration, the filter residue was extracted with hot water, the extract evaporated on the rotary evaporator, and the oil remaining brought to crystallization by addition of diethyl ether. The crystals were filtered off with suction, and dried for 24 hours at 50° C. under reduced pressure.

There were obtained in this manner 0.57 grams (81% of theory) of D,L-serine hydrochloride having a melting point of 140°–145° C. (Literature: 140°–142° C.), The elemental analysis resulted in the consistent values. $C_3H_8ClNO_3$ (141.56)
Calculated: C: 25.46%; H: 5.70%; Cl: 25.05%; N: 9.89%; Found: C: 25.48%; H: 5.56%; Cl: 24.87%; N: 9.76%.

The D,L-serine hydrochloride is pure by thin layer chromatography.

EXAMPLE 5

1.56 grams (0.005 mole) of 2-azido-3-benzyloxypropionic acid benzyl ester were dissolved in 10 ml of absolute acetone, 0.30 grams (0.008 mole) of dry hydrogen chloride gas led in, and 0.2 grams of palladium on activated carbon (10%) added. It was subsequently hydrogenated in an autoclave for 20 hours at a hydrogen pressure of 20 bar and a reaction temperature of 25° C. After filtration, the filter residue was extracted with hot water, the extract evaporated on a rotary evaporator, and the oily residue neutralized with ammonia. After addition of 25 ml of ethanol, the mixture was cooled to 0° C. The thus precipitated D,L-serine was filtered off with suction, and dried for 24 hours at 50° C. under reduced pressure.

There were obtained 0.47 grams (90% of theory) of D,L-serine having a melting point of 224°–226° C. (Literature: 228°–236° C.).

The D,L-serine is pure by thin layer chromatography.

EXAMPLE 6

1.56 grams (0.005 mole) of 2-azido-3-benzyloxypropionic acid benzyl ester were dissolved in 10 ml of absolute ethanol, and treated with 0.20 grams of palladium on activated carbon (10%). This reaction mixture was hydrogenated in an autoclave for 25 hours at 40 bar hydrogen pressure and a reaction temperature of 50° C. Then there were added 5 ml of water and a further 0.1 grams of palladium/activated carbon and subsequently hydrogenation continued for 24 hours at 50 bar hydrogen pressure and a reaction temperature of 70° C.

After filtration, the filtrate was evaporated to dryness and the solid residue dried for 24 hours at 50° C. under reduced pressure. These were obtained 0.51 grams (97% of theory) of D,L-serine having a melting point of 229°–231° C. (Literature: 228°–236° C.).

The D,L-serine is pure by thin layer chromatography.

EXAMPLE 7

1.56 grams (0.005 mole) of 2-azido-3-benzyloxypropionic acid benzyl ester were dissolved in 10 ml of absolute methanol, 0.70 grams (0.019 mole) of dry hydrogen chloride gas led in, and the mixture treated with 0.20 grams of palladium on activated carbon (10%).

This reaction mixture was hydrogenated in an autoclave for 25 hours at 25° C., and a hydrogen pressure of 20 bar. After filtration, the filtrate was concentrated on a rotary evaporator, and the residue recrystallized from methanol/diethyl ether (volume ratio about 1:1).

There were obtained 0.75 grams (96% of theory) of D,L-serine methyl ester hydrochloride having a melting point of 131°–133° C. (Literature: 131°–134° C.).

EXAMPLE 8

1.56 grams (0.005 mole) of 2-azido-3-benzyloxypropionic acid benzyl ester were dissolved in 10 ml of absolute ethanol, 1.10 grams (0.03 mole) of dry hydrogen chloride led in, and the mixture treated with 0.20 grams of palladium on activated carbon (10%). This reaction mixture was hydrogenated in an autoclave for 40 hours at 25° C., and a hydrogen pressure of 20 bar. After filtration, the filtrate was concentrated on the rotary evaporator, and the residue recrystallized from ethanol/diethyl ether (volume ratio about 1:1). There were obtained 0.81 grams (96% of theory) of D,L-serine ethyl ester hydrochloride having a melting point of 102°–103.5° C. (Literature: 100°–102° C.

EXAMPLE 9

1.56 grams (0.005 mole) of 2-azido-3-benzyloxypropionic acid benzyl ester were dissolved in 10 ml of ethanol, 1.50 grams (0.041 mole) of dry hydrogen chloride gas led in and 0.03 grams of rhenium (VII) sulfide added. This reaction mixture was hydrogenated in an autoclave for 20 hours at 25° C. and a hydrogen pressure of 20 bar. After filtering off the catalyst the solvent was vaporized. The oil obtained (1.42 grams = 88% of crude O-benzyl-D,L-serine benzyl ester hydrochloride) was dissolved in chloroform and treated with diethyl ether. The precipitated crystals were recrystallized three times from ethanol/diethyl ether. There was obtained 0.78 grams (48% of theory) of O-benzyl-D,L-serine benzyl ester hydrochloride having a melting point of 144.5°–145.5° C. (literature: 147.5°–148.5° C.).

EXAMPLE 10

1.56 grams (0.005 mole) of 2-azido-3-benzyloxypropionic acid benzyl ester were dissolved in 10 ml of absolute ethanol and there was added 0.20 grams of palladium on activated carbon (10%). Hydrogen was led into the vigorously stirred suspension for 8 hours through a frit. Then, the mixture was filtered, the filtrate discarded and the filter residue extracted with hot water. The extract was concentrated on a rotary evaporator, the precipitated product separated off and dried for 24 hours at 50° C. under reduced pressure.

There were obtained 0.77 grams (79% of theory) of O-benzyl-D,L-serine having a melting point of 202°–205° C., (Literature: 218° C.)

EXAMPLE 11

1.56 grams (0.005 mole) of 2-azido-3-benzyloxypropionic acid benzyl ester were hydrogenated according to Example 10, but in an autoclave at 25° C. for 20 hours under 30 bar hydrogen pressure.

After working up there were obtained 0.80 grams (82% of theory) of O-benzyl-D,L-serine having a melting point of 205°–207° C.

What is claimed is:

1. 2-azido-3-benzyloxypropionic acid benzyl ester.
2. A process for the production of the 2-azido-3-benzyloxypropionic acid benzyl ester of claim 1 comprising (1) reacting 2-chloro-acrylonitrile with double the molar amount of benzyl alcohol to form 3-benzyloxy-2-chloropropionic acid iminobenzyl ester, (2), saponifying this compound with acid to form 3-benzyloxy-2-chloropropionic acid benzyl ester and (3) then exchanging the chlorine atom for an azido group by reacting with an alkali metal azide in the presence of a phase transfer catalyst.
3. A process according to claim 2, wherein in step (1) there is employed 2.1 to 10 moles of benzyl alcohol per mole of 2-chloroacrylonitrile in the presence of 0.5 to 50 mole percent of an alkali metal benzylate catalyst based on the amount of 2-chloroacrylontrile at a temperature of −35° to +80° C., in step (2) the saponification is in the presence of a mineral acid and in step (3) the reaction is carried out between room temperature and 100° C., the phase transfer catalyst is a quaternary ammonium salt, a phosphonium salt or a crown ether and the alkali metal azide is used in a 1.1 to 1.5 times the theoretically required amount.
4. A process according to claim 3, wherein the azide is sodium azide and the phase transfer catalyst is a quaternary ammonium salt.

* * * * *